(12) United States Patent
Dhar et al.

(10) Patent No.: US 10,633,339 B2
(45) Date of Patent: *Apr. 28, 2020

(54) TRICYCLIC SULFONE COMPOUND AS A ROR GAMMA MODULATOR

(71) Applicant: BRISTOL-MYERS SQUIBB COMPANY, Princeton, NJ (US)

(72) Inventors: T. G. Murali Dhar, Newtown, PA (US); Zili Xiao, East Windsor, NJ (US); Michael G. Yang, Narberth, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/413,673

(22) Filed: May 16, 2019

(65) Prior Publication Data

US 2019/0352261 A1 Nov. 21, 2019

Related U.S. Application Data

(60) Provisional application No. 62/672,802, filed on May 17, 2018.

(51) Int. Cl.
 *C07D 209/80* (2006.01)
 *A61P 37/02* (2006.01)
(52) U.S. Cl.
 CPC .......... *C07D 209/80* (2013.01); *A61P 37/02* (2018.01)
(58) Field of Classification Search
 None
 See application file for complete search history.

(56) References Cited

FOREIGN PATENT DOCUMENTS

WO WO2016179460 A1 11/2016

OTHER PUBLICATIONS

Schafer, S., Kolkhof, P. Failure is an option: learning from unsuccessful proof-of-concept trials. Drug Discovery Today. Nov. 2008, 13, 913-916.*
Horig, H., Pullman, W. From bench to clinic and back: Perspective on the 1st IQPC Translational Research conference. Journal of Translational Medicine. Dec. 2004, 2, 44.*
Kargbo R. B. ROR(Gmma)T Modulating Activity for the Treatment of Cancer. ACS Medicinal Chemistry Letters, 2018, 9, 590-591.*
Chang et al., The therapeutic potential of RORγ modulators in the treatment of human disease. Journal of Experimental Pharmacology, 2012, 4, 141-148.*
U.S. Appl. No. 15/148,209, filed May 6, 2016, Granted U.S. Pat. No. 9,815,859.
U.S. Appl. No. 15/701,818, filed Sep. 12, 2017, Granted U.S. Pat. No. 10,273,259.
PCT/US2017/055687, Oct. 9, 2017, Published WO2018/071314.
PCT/US2017/056257, Oct. 12, 2017, Published WO2018/071620.
PCT/US2017/060501, Nov. 8, 2017, Published WO2018/089402.
U.S. Appl. No. 15/806,554, filed Nov. 8, 2017, Published US20180127368A1.

* cited by examiner

*Primary Examiner* — Po-Chih Chen
(74) *Attorney, Agent, or Firm* — Elliott Korsen

(57) ABSTRACT

There is described a RORγ modulator of the formula (I),

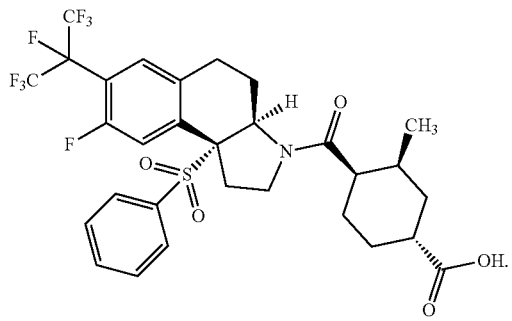

or stereoisomers, pharmaceutically acceptable salts, solvates, or prodrugs thereof. Also provided are pharmaceutical compositions comprising the same. The compound of the invention may be useful in methods for modulating RORγ activity in a cell and methods for treating a subject suffering from a disease or disorder in which the subject would therapeutically benefit from modulation of RORγ activity, for example, autoimmune and/or inflammatory disorders.

5 Claims, No Drawings

TRICYCLIC SULFONE COMPOUND AS A ROR GAMMA MODULATOR

CROSS-REFERENCE TO RELATED APPLICATIONS

This application claims the benefit of U.S. Provisional Application No. 62/672,802, filed May 17, 2018, the disclosure of which is incorporated herein by reference in its entirety.

FIELD OF THE INVENTION

This invention relates to a modulator of the retinoid-related orphan receptor RORγ and methods for using said modulator. The compound described herein can be particularly useful for treating a variety of diseases and disorders in humans and animals. Exemplary disorders include, but are not limited to, psoriasis, rheumatoid arthritis, inflammatory bowel disease, Crohn's disease, ulcerative colitis, acute graft-versus-host disease, psoriatic arthritis, ankylosing spondylitis, systemic lupus erythematosus (SLE), lupus nephritis (LN), Sjögren's syndrome and multiple sclerosis.

BACKGROUND OF THE INVENTION

The retinoid-related orphan receptors, RORα, RORβ, and RORγ, play an important role in numerous biological processes including organ development, immunity, metabolism, and circadian rhythms. See, for example, Dussault et al. in Mech. Dev. (1998) vol. 70, 147-153; Andre et al. in EMBO J. (1998) vol. 17, 3867-3877; Sun et al. in Science (2000) vol. 288, 2369-2373; and Jetten in Nucl. Recept. Signal. (2009) vol. 7, 1-32.

RORγ is expressed in several tissues including the thymus, kidney, liver, and muscle. Two isoforms of RORγ have been identified: RORγ1 and RORγ2 (also known, respectively, as RORγ and RORγt). See, for example, Hirose et al. in Biochem. Biophys. Res. Commun. (1994) vol. 205, 1976-1983; Oritz et al. in Mol. Endocrinol. (1995) vol. 9, 1679-1691; and He et al. in Immunity (1998) vol. 9, 797-806. Expression of RORγt is restricted to lymphoid cell types including CD4+CD8+ thymocytes, IL-17 producing T helper (Th17) cells, lymphoid tissue inducer (LTi) cells, and γδ cells. RORγt is essential for the development of lymph nodes and Peyer's patches and for the normal differentiation of Th17, γδ, and LTi cells. See, for example, Sun et al. in Science (2000) vol. 288, 2369-2373; Ivanov et al. in Cell (2006) vol. 126, 1121-1133; Eberl et al. in Nat. Immunol. (2004) vol. 5, 64-73; Ivanov et al. in Semin. Immunol. (2007) vol. 19, 409-417; and Cua and Tato in Nat. Rev. Immunol. (2010) vol. 10, 479-489.

Proinflammatory cytokines such as IL-17A (also referred to as IL-17), IL-17F, and IL-22 produced by Th17 cells and other RORγ+ lymphocytes activate and direct the immune response to extracellular pathogens. See, for example, Ivanov et al. in Semin. Immunol. (2007) vol. 19: 409-417; and Marks and Craft in Semin. Immunol. (2009) vol. 21, 164-171. RORγ directly regulates IL-17 transcription and disruption of RORγ in mice attenuates IL-17 production. See, for example, Ivanov et al. in Cell (2006) vol. 126, 1121-1133.

Dysregulated production of IL-17 has been implicated in several human autoimmune and inflammatory diseases including multiple sclerosis, rheumatoid arthritis, psoriasis, inflammatory bowel disease (IBD), Systemic lupus erythematosus (SLE) and lupus nephritis (LN), Sjögren's syndrome and asthma. See, for example, Lock et al. in Nat. Med. (2002) vol. 8, 500-508; Tzartos et al. in Am. J. Pathol. (2008) vol. 172, 146-155; Kotake et al. in J. Clin. Invest. (1999) vol. 103, 1345-1352; Kirkham et al. in Arthritis Rheum. (2006) vol. 54, 1122-1131; Lowes et al. in J. Invest. Dermatol. (2008) vol. 128, 1207-1211; Leonardi et al. in N. Engl. J. Med. (2012) vol. 366, 1190-1199; Fujino et al. in Gut (2003) vol. 52, 65-70; Seiderer et al. in Inflamm. Bowel Dis. (2008) vol. 14, 437-445; Wong et al. in Clin. Exp. Immunol. (2001) vol. 125, 177-183; Duo Li et al. in Autoimmunity (2015) vol. 48, 353-361, M. Tahara et al. in Clinical and Experimental Immunology (2016), Vol. 187, 213-224 and Agache et al. in Respir. Med. (2010) 104: 1131-1137. In murine models of these diseases, inhibition of IL-17 function by neutralizing antibodies or genetic disruption of IL-17 or IL-17 receptor ameliorates the disease course or clinical symptoms. See, for example, Hu et al. in Ann. N.Y. Acad. Sci. (2011) vol. 1217, 60-76.

Disruption of RORγ in mice also attenuates disease progression or severity in animal models of autoimmunity and inflammation including experimental autoimmune encephalomyelitis (EAE), imiquimod induced psoriasis, colitis, Systemic lupus erythematosus (SLE) and lupus nephritis (LN), Sjögren's syndrome and allergic airway disease. See, for example, Ivanov et al. in Cell (2006) vol. 126, 1121-1133; Yang et al. in Immunity (2008) vol. 28, 29-39; Pantelyushin et al. in J. Clin. Invest. (2012) vol. 122, 2252-2256; Leppkes et al. in Gastroenterology (2009) vol. 136, 257-267; A. Gaweco et al. Annals of the Rheumatic Diseases (2015), 74, 120; M. Tahara et al. in Clinical and Experimental Immunology (2016), Vol. 187, 213-224 and Tilley et al. in J. Immunol. (2007) vol. 178, 3208-3218.

Each of the references in this Background section is hereby incorporated herein by reference in its entirety for all purposes.

Therapeutic agents exist to treat a variety of inflammatory and autoimmune diseases, but there still remains a significant unmet medical need in these therapeutic areas. Given the role of IL-17 in human disease and the validation of IL-17 and RORγ as targets in murine disease models, compounds capable of modulating RORγt activity are contemplated to provide a therapeutic benefit in the treatment of multiple immune and inflammatory disorders.

The compound of the invention has been found to be capable of modulating RORγt activity while not forming a GSH adduct based on in vitro experiments. Formation of a GSH adduct may not be a desirable characteristic because of the potential formation of metabolites.

SUMMARY OF THE INVENTION

In one aspect, the invention comprises the compound of the formula (I),

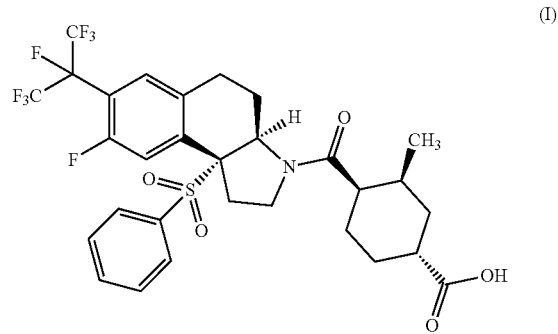 [SMILES: C[C@H]1C[C@H](C(=O)O)CC[C@H]1C(=O)N1CC[C@@]2(S(=O)(=O)c3ccccc3)c3cc(F)c(C(F)(C(F)(F)F)C(F)(F)F)cc3CC[C@@H]12]

or pharmaceutically acceptable salts thereof. The invention includes stereoisomers, solvates or prodrugs thereof.

In one aspect, the invention comprises the compound of the formula (I),

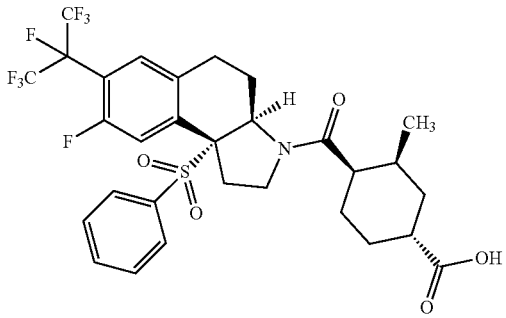

(I)

In another aspect, the invention comprises pharmaceutical compositions comprising the compound according to formula (I), stereoisomeric form or a pharmaceutically acceptable salt, as described herein, and a pharmaceutically acceptable carrier, excipient, or diluent.

In another aspect, the invention comprises methods for modulating RORγ in a cell comprising contacting the cell with an effective amount of the compound according to formula (I), stereoisomeric form or a pharmaceutically acceptable salt, as described herein. This aspect may be conducted in vitro or in vivo.

In another aspect, the invention comprises methods for treating a subject suffering from a disease or disorder modulated by RORγ, the method comprising administering to a subject a therapeutically effective amount of the compound according to formula (I), or a stereoisomeric form, pharmaceutically acceptable salt or pharmaceutical composition as described herein.

In another aspect, the invention comprises a method for treating a disease or disorder selected from an inflammatory disease or disorder, an autoimmune disease or disorder, an allergic disease or disorder, a metabolic disease or disorder, and/or cancer in a subject, the method comprising administering to the subject a therapeutically effective amount of the compound according to formula (I), or a stereoisomeric form, pharmaceutically acceptable salt or pharmaceutical composition as described herein.

DETAILED DESCRIPTION OF THE INVENTION

In one aspect, the invention comprises the compound of formula (I),

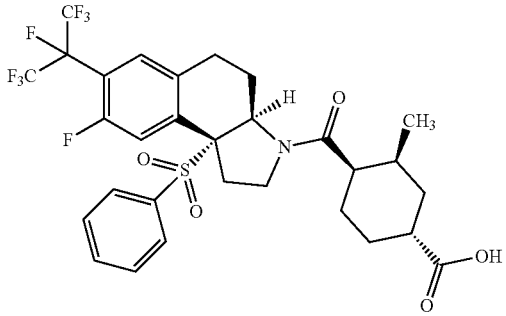

(I)

or a stereoisomer or pharmaceutically acceptable salt thereof.

In one embodiment, the invention provides a pharmaceutical composition, comprising a pharmaceutically acceptable carrier and a therapeutically effective amount of the compound of the invention or a stereoisomer, a pharmaceutically acceptable salt or a solvate thereof.

In another embodiment, the invention provides a process for making the compound of the invention or a stereoisomer, pharmaceutically acceptable salt or a solvate thereof.

In another embodiment, the invention provides the compound of the present invention for use in therapy.

In another embodiment, the invention provides a combined preparation of the compound of the present invention and additional therapeutic agent(s) for simultaneous, separate or sequential use in therapy.

In another embodiment, the invention provides the compound of the present invention for use in treating diseases (or a method of treating diseases) in which inflammation is a component including, without limitation, diseases such as psoriasis, rheumatoid arthritis, inflammatory bowel disease, Crohn's disease, ulcerative colitis, acute graft-versus-host disease, psoriatic arthritis, ankylosing spondylitis and multiple sclerosis.

The following are definitions of terms used in this specification and appended claims. The initial definition provided for a group or term herein applies to that group or term throughout the specification and claims, individually or as part of another group, unless otherwise indicated.

The compound of formula I may exist in a free form (with no ionization) or can form salts which are also within the scope of this invention. Unless otherwise indicated, reference to an inventive compound is understood to include reference to the free form and to salts thereof. The term "salt(s)" denotes basic salt(s) formed with inorganic and/or organic bases. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus are contemplated within the scope of the invention. Salts of the compound of formula I may be formed, for example, by reacting the compound of the formula I with an amount of base, such as an equivalent amount, in a medium such as one in which the salt precipitates or in an aqueous medium followed by lyophilization.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, ephenamine, N,N'-dibenzylethylene-diamine, dehydroabietylamine, N-ethylpiperidine, benzylamine, dicyclohexylamine or similar pharmaceutically acceptable amines and salts with amino acids such as arginine, lysine and the like.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compound wherein the parent compound is modified by making base salts thereof.

Examples of pharmaceutically acceptable salts include, but are not limited to, alkali or organic salts of the carboxylic acid. The pharmaceutically acceptable salts include the conventional non-toxic salts or the quaternary ammonium salts of the parent compound formed, for example, from non-toxic inorganic or organic bases.

The pharmaceutically acceptable salts of the present invention can be synthesized from the parent compound, which contains an acidic moiety, by conventional chemical methods. Generally, such salts can be prepared by reacting the free acid form of the compound with a stoichiometric amount of the appropriate base in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th Edition, Mack Publishing Company, Easton, Pa. (1990), the disclosure of which is hereby incorporated by reference.

Prodrugs and solvates of the inventive compound are also contemplated. The term "prodrug" denotes a compound which, upon administration to a subject, undergoes chemical conversion by metabolic or chemical processes to yield the compound of formula I, and/or a salt and/or solvate thereof. Any compound that will be converted in vivo to provide the bioactive agent (i.e., the compound for formula I) is a prodrug within the scope and spirit of the invention. For example, the carboxylic acid group of the compound of formula I can form physiologically hydrolyzable esters which serve as prodrugs by being hydrolyzed in the body to yield the compound of formula I per se. Such prodrugs are preferably administered orally since hydrolysis in many instances occurs principally under the influence of digestive enzymes. Parenteral administration may be used where the ester per se is active, or in those instances where hydrolysis occurs in the blood. Examples of physiologically hydrolyzable esters of compounds of formula I include $C_{1-6}$ alkylbenzyl, 4-methoxybenzyl, indanyl, phthalyl, methoxymethyl, $C_{1-6}$ alkanoyloxy-$C_{1-6}$ alkyl, e.g., acetoxymethyl, pivaloyloxymethyl or propionyloxymethyl, $C_{1-6}$ alkoxycarbonyloxy-$C_{1-6}$ alkyl, e.g., methoxycarbonyloxymethyl or ethoxycarbonyloxymethyl, glycyloxymethyl, phenylglycyloxymethyl, (5-methyl-2-oxo-1,3-dioxolen-4-yl)-methyl and other well-known physiologically hydrolyzable esters used, for example, in the penicillin and cephalosporin arts. Such esters may be prepared by conventional techniques known in the art.

Various forms of prodrugs are well known in the art. For examples of such prodrug derivatives, see:
a) Bundgaard, H., ed., *Design of Prodrugs*, Elsevier (1985), and Widder, K. et al., eds., *Methods in Enzymology*, 112:309-396, Academic Press (1985);
b) Bundgaard, H., Chapter 5, "Design and Application of Prodrugs", Krosgaard-Larsen, P. et al., eds., *A Textbook of Drug Design and Development*, pp. 113-191, Harwood Academic Publishers (1991); and
c) Bundgaard, H., *Adv. Drug Deliv. Rev.*, 8:1-38 (1992), each of which is incorporated herein by reference.

Another aspect of the invention is a pharmaceutical composition including the compound, or a pharmaceutical salt or solvate thereof, as described herein. The pharmaceutical compositions described herein generally comprise a combination of the compound described herein and a pharmaceutically acceptable carrier, diluent, or excipient. Such compositions are substantially free of non-pharmaceutically acceptable components, i.e., contain amounts of non-pharmaceutically acceptable components lower than permitted by U.S. regulatory requirements at the time of filing this application. In some embodiments of this aspect, if the compound is dissolved or suspended in water, the composition further optionally comprises an additional pharmaceutically acceptable carrier, diluent, or excipient. In other embodiments, the pharmaceutical compositions described herein are solid pharmaceutical compositions (e.g., tablets, capsules, etc.).

These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer, intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Also, pharmaceutical compositions can contain, as the active ingredient, the compound described herein above in combination with one or more pharmaceutically acceptable carriers. In making the compositions described herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions described herein can be formulated so as to provide quick, sustained or delayed release of the active ingredient after administration to the subject by employing procedures known in the art.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual subject, the severity of the subject's symptoms, and the like.

For preparing solid compositions such as tablets, the principal active ingredient is mixed with a pharmaceutical excipient to form a solid preformulation composition containing a homogeneous mixture of a compound described herein. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of a compound described herein.

The tablets or pills can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compound and compositions can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a subject will vary depending upon what is being administered, the purpose of the administration, such as prophylaxis or therapy, the state of the subject, the manner of administration, and the like. In therapeutic applications, compositions can be administered to a subject already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the subject, and the like.

The compositions administered to a subject can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutically acceptable salts.

The therapeutic dosage of the compound can vary according to, for example, the particular use for which the treatment is made, the manner of administration of the compound, the health and condition of the subject, and the judgment of the prescribing physician. The proportion or concentration of a compound described herein in a pharmaceutical composition can vary depending upon a number of factors including dosage, chemical characteristics (e.g., hydrophobicity), and the route of administration. For example, the compound described herein can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular subject, the biological efficacy of the compound, formulation of the excipient, and its route of administration. Effective doses can be extrapolated from dose-response curves derived from in vitro or animal model test systems.

The compound of the present invention is useful to prevent, diagnose, and treat various medical disorders in humans or animals. The compound is used to inhibit or reduce one or more activities associated with RORγ receptors, relative to RORγ receptors in the absence of the same compound. Thus, in one aspect of the invention, a method for treating a disease or disorder selected from an autoimmune disease or disorder, asthma, an allergic disease or disorder, a metabolic disease or disorder, and cancer in a subject comprises administering to the subject a therapeutically effective amount of the compound of formula (I), or a pharmaceutically acceptable salt, solvate, or pharmaceutical composition as described herein. See, e.g., L. A. Solt et al., "Action of RORs and their ligands in (patho)physiology," *Trends Endocrinol. Metab.* 2012, 23 (12): 619-627; M. S. Maddur et al., "Th17 cells: biology, pathogenesis of autoimmune and inflammatory diseases, and therapeutic strategies," *Am. J. Pathol.* 2012 July; 181(1):8-18; and A. M. Jetten, "Retinoid-related orphan receptors (RORs): critical roles in development, immunity, circadian rhythm, and cellular metabolism," *Nucl. Recept. Signal.* 2009; 7:e003, each of which is hereby incorporated herein by reference in its entirety, as well as the references discussed in the Background section. In certain embodiments, the autoimmune disease or disorder is selected from rheumatoid arthritis, ankylosing spondylitis, psoriasis and psoriatic arthritis, multiple sclerosis, inflammatory bowel diseases Sjögren's syndrome and lupus. In certain embodiments, the allergic disease or disorder is selected from allergic rhinitis and dermatitis. In certain embodiments, the metabolic disease or disorder is selected from obesity, obesity-induced insulin resistance and type II diabetes.

In certain embodiments, the disease or disorder is rheumatoid arthritis.

In other embodiments, the disease or disorder is multiple sclerosis.

In other embodiments, the disease or disorder is ankylosing spondylitis.

In other embodiments, the disease or disorder is inflammatory bowel disease.

In other embodiments, the disease or disorder is lupus.

In other embodiments, the disease or disorder is Sjögren's syndrome.

In other embodiments, the disease or disorder is psoriasis.

In other embodiments, the disease or disorder is psoriatic arthritis.

In other embodiments, the disease or disorder is graft-vs.-host disease (GVHD).

In other embodiments, the disease or disorder is autoimmune uveitis.

In other embodiments, the disease or disorder is obesity and/or insulin resistance.

In other embodiments, the disease or disorder is melanoma.

In certain aspects, the medical disorder being diagnosed, treated, or prevented by use of the presently disclosed compound can be, for example, an autoimmune disorder. In other embodiments, the disorder being diagnosed, treated or prevented by use of the presently disclosed compound can be an inflammatory disorder. For example, in certain embodiments, the disorder is selected from arthritis, diabetes, multiple sclerosis, uveitis, rheumatoid arthritis, psoriasis, asthma, bronchitis, allergic rhinitis, chronic obstructive pulmonary disease, atherosclerosis, *H. pylori* infection and inflammatory bowel disease. In other embodiments, the disorder is selected from Crohn's disease, ulcerative colitis, sprue and food allergies. In other embodiments, the disorder is autoimmune encephalomyelitis, imiquimod-induced psoriasis, colitis or allergic airway disease.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

In certain embodiments, a therapeutically effective amount can be an amount suitable for (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder; or (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

As used here, the terms "treatment" and "treating" means (i) ameliorating the referenced disease state, for example, ameliorating a disease, condition or disorder in an individual who is experiencing or displaying the pathology or symptomatology of the disease, condition or disorder (i.e., reversing or improving the pathology and/or symptomatology) such as decreasing the severity of disease; (ii) eliciting the biological or medicinal response that is being sought in a tissue, system, animal, individual or human by a researcher, veterinarian, medical doctor or other clinician; or (iii) inhibiting the referenced disease state; for example, inhibiting a disease, condition or disorder in an individual who is experiencing or displaying the pathology or symptomatology of the disease, condition or disorder.

Method of Preparation

The compound of the present invention may be synthesized by many methods available to those skilled in the art of organic chemistry. One example of a method of preparation is shown in the Example below. Different methods to prepare the compound of the present invention will be evident to those skilled in the art. Frequently chemists skilled in the art of synthesis may devise alternative preparations which may be desirable based on one or more considerations such as shorter reaction time, less expensive starting materials, ease of operation or isolation, improved yield, suitability to catalysis, avoidance of toxic reagents, accessibility of specialized instrumentation, decreased number of linear steps, etc.

Preparation of a homochiral compound or intermediate may be carried out by techniques known to one skilled in the art. For example, a homochiral compound may be prepared by separation of racemic products or diastereomers by chiral phase preparative chromatography. Alternatively, the compound may be prepared by methods known to give enantiomerically or diastereomerically enriched products. The reactions and techniques used to prepare the compound of the present invention are performed in solvents appropriate to the reagents and materials employed and are suitable for the transformations being effected. All reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art, with alternatives required when incompatible substituents are present. This will sometimes require a judgment to modify the order of the synthetic steps or to select one particular process scheme over another in order to obtain the desired compound of the invention. It will also be recognized that another major consideration in the planning of any synthetic route in this field is the judicious choice of a protecting group used for protection of reactive functional groups present in the compounds described in this invention. An authoritative account describing the many alternatives to the trained practitioner is Wuts and Greene, *Greene's Protective Groups in Organic Synthesis*, Fourth Edition, Wiley and Sons (2007).

EXAMPLES

The following examples illustrates the particular and preferred embodiments of the present invention and do not limit the scope of the present invention. A synthetic scheme for preparing the compound of the present invention is described below. This scheme is illustrative and is not meant to limit the possible techniques one skilled in the art may use to prepare the compound disclosed herein. Chemical abbreviations and symbols as well as scientific abbreviations and symbols have their usual and customary meanings unless otherwise specified. Additional abbreviations employed in the Examples and elsewhere in this application are defined below.

Column chromatography was generally performed with pre-packed silica gel cartridges using a CombiFlash® automated chromatography apparatus (Teledyne Isco), eluting with the solvent or solvent mixture indicated. Analytical high performance liquid chromatography (HPLC) was performed using a reverse phase column of a size appropriate to the quantity of material being separated, generally eluting with a gradient of increasing concentration of acetonitrile in water, also containing 0.05% trifluoroacetic acid, at a rate of elution suitable to the column size and separation to be achieved. Chiral super-critical fluid chromatographic (SFC) separation of enantiomers or diastereomers was performed using conditions indicated. Mass spectral data were obtained by liquid chromatography mass spectroscopy (LCMS) using electrospray ionization.

Chemical names were determined using ChemBioDraw Ultra, version 14.0.0.126 (PerkinElmer Inc.). The following abbreviations are used:

| ABBREVIATION | NAME |
|---|---|
| BF$_4$NO | Nitrosyl tetrafluoroborate |
| DCM | dichloromethane |
| EtOAc | ethyl acetate |
| h | hours |
| HATU | O-(7-azabenzotriazol-l-yl)-1,1,3,3-tetramethyluronium hexafluorophosphate |
| HPLC | high performance liquid chromatography |
| LCMS | liquid chromatography-mass spectrometry |
| MeCN | acetonitrile |
| MeOH | methanol |
| min | minutes |
| rt | room temperature |
| SFC | super-critical fluid chromatography |
| THF | tetrahydrofuran |
| $t_R$ | chromatographic retention time |

Preparation of the Compound of Formula I (Compound 1)

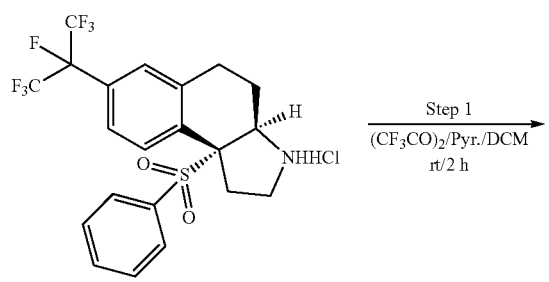

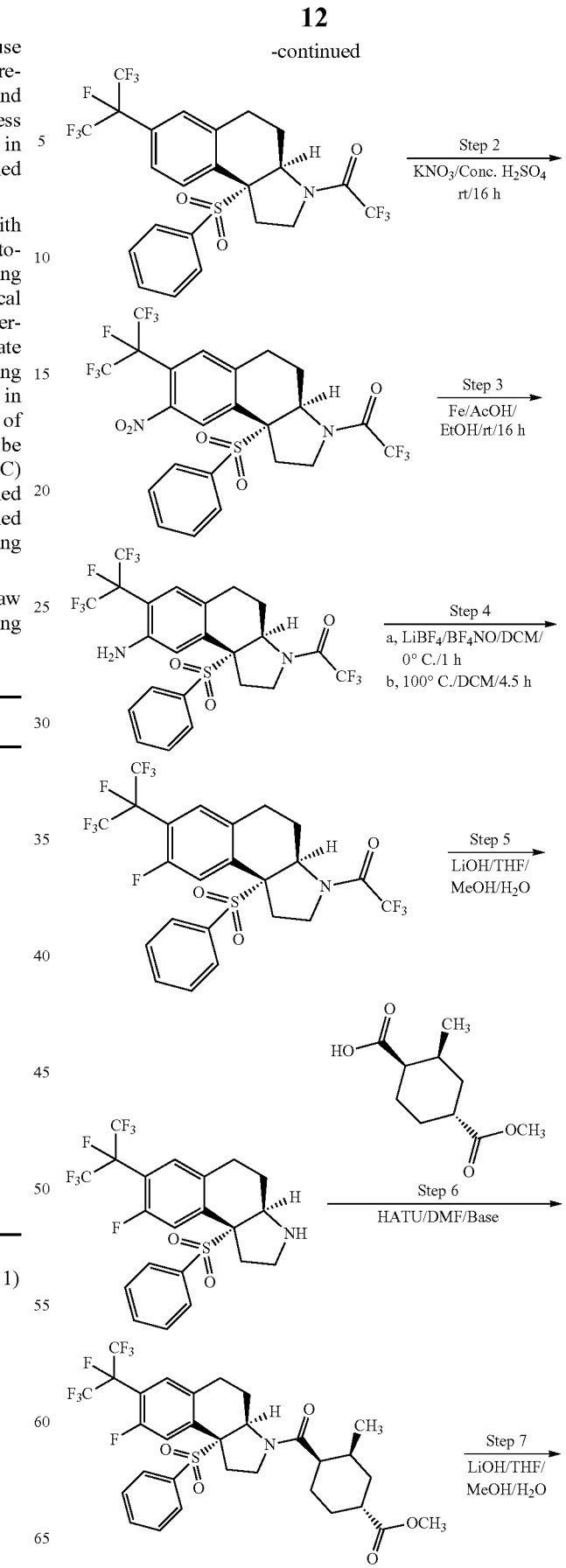

-continued

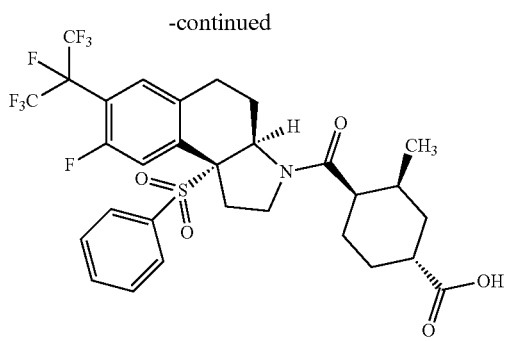

Example 1

(1R,3S,4R)-4-((3aR,9bR)-8-fluoro-7-(perfluoropropan-2-yl)-9b-(phenylsulfonyl)-2,3,3a,4,5,9b-hexahydro-1H-benzo[e]indole-3-carbonyl)-3-methylcyclohexane-1-carboxylic acid

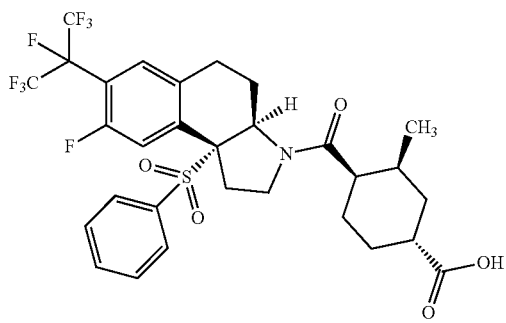 [SMILES: C[C@H]1C[C@H](C(=O)O)CC[C@H]1C(=O)N1CC[C@@]2(S(=O)(=O)c3ccccc3)c3cc(F)c(C(F)(C(F)(F)F)C(F)(F)F)cc3CC[C@@H]12]

Step 1: Preparation of 2,2,2-trifluoro-1-((3aR,9bR)-7-(perfluoropropan-2-yl)-9b-(phenylsulfonyl)-1,2,3a,4,5,9b-hexahydro-3H-benzo[e]indol-3-yl)ethan-1-one

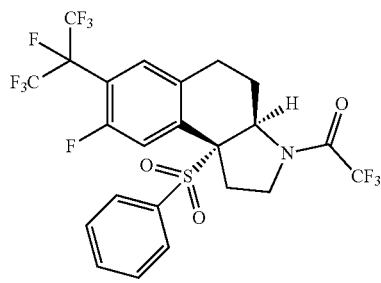 [SMILES: O=C(N1CC[C@@]2(S(=O)(=O)c3ccccc3)c3cc(F)c(C(F)(C(F)(F)F)C(F)(F)F)cc3CC[C@@H]12)C(F)(F)F]

To a solution of (3aR,9bR)-7-(perfluoropropan-2-yl)-9b-(phenylsulfonyl)-2,3,3a,4,5,9b-hexahydro-1H-benzo[e]indole hydrochloride (International Patent Application WO 2016/179460, 1.78 g, 3.44 mmol) in DCM (20 mL) cooled in an ice-water bath was added pyridine (1.39 mL, 17.2 mmol) followed by 2,2,2-trifluoroacetic anhydride (0.717 mL, 5.16 mmol). The mixture was stirred at rt for 1 h. The reaction mixture was diluted with DCM (40 mL), washed sequentially with 0.2 N HCl (2×50 mL), water (2×40 mL), and brine (50 mL), dried and concentrated to give 2,2,2-trifluoro-1-((3aR,9bR)-7-(perfluoropropan-2-yl)-9b-(phenylsulfonyl)-1,2,3a,4,5,9b-hexahydro-3H-benzo[e]indol-3-yl)ethan-1-one as a yellow solid (1.9 g, 96% yield) which was used in the next step without further purification.

Steps 2 and 3: Preparation of 1-((3aR,9bR)-8-amino-7-(perfluoropropan-2-yl)-9b-(phenylsulfonyl)-1,2,3a,4,5,9b-hexahydro-3H-benzo[e]indol-3-yl)-2,2,2-trifluoroethan-1-one

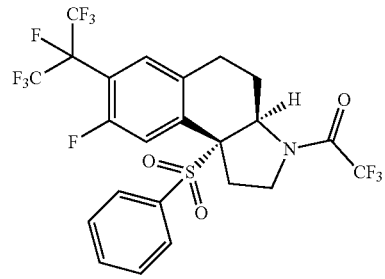 [SMILES: O=C(N1CC[C@@]2(S(=O)(=O)c3ccccc3)c3cc(F)c(C(F)(C(F)(F)F)C(F)(F)F)cc3CC[C@@H]12)C(F)(F)F]

To a solution of 2,2,2-trifluoro-1-43aR,9bR)-7-(perfluoropropan-2-yl)-9b-(phenylsulfonyl)-1,2,3a,4,5,9b-hexahydro-3H-benzo[e]indol-3-yl)ethan-1-one (2.50 g, 4.33 mmol) dissolved in $H_2SO_4$ (95%, 40 mL) was added $KNO_3$ (0.700 g, 6.93 mmol) in portions at 0° C. The mixture was slowly warmed to rt and stirred at rt for 18 h. The reaction mixture was added to ice water (150 mL) and extracted with EtOAc (2×100 mL). The organic layer was washed sequentially with water (2×80 mL) and brine (80 mL), dried ($Na_2SO_4$) and concentrated to afford the crude product. Ethanol (20 mL), was added, and after stirring for 1 h the brown solid was collected by filtration and used without further purification.

The above solid was mixed with ethanol (30 mL) and acetic acid (20 mL), iron powder (1.21 g, 21.7 mmol) was added, and the mixture was stirred at rt for 18 h. The reaction mixture was filtered through a pad of Celite and the filter cake was washed with EtOAc (2×20 mL). The filtrate was concentrated under reduced pressure, diluted with water (100 mL) and EtOAc (100 mL) and made basic with solid $Na_2CO_3$. The organic layer was separated, the aqueous layer was extracted with EtOAc (50 mL), and the combined organic layers were dried ($Na_2SO_4$) and concentrated. The residue was purified by column chromatography on silica gel (80 g), eluting with DCM, to yield 1-((3aR,9bR)-8-amino-7-(perfluoropropan-2-yl)-9b-(phenylsulfonyl)-1,2,3a,4,5,9b-hexahydro-3H-benzo[e]indol-3-yl)-2,2,2-trifluoroethan-1-one (1.70 g, 66% yield). $^1$H NMR (500 MHz, chloroform-d) δ 7.57 (tt, J=7.3, 1.4 Hz, 1H), 7.41-7.31 (m, 4H), 7.20 (s, 1H), 6.79 (br s, 1H), 4.77 (dd, J=11.9, 5.0 Hz, 1H), 4.42 (br s, 2H), 4.22-4.14 (m, 1H), 3.97-3.89 (m, 1H), 3.61-3.53 (m, 1H), 2.62 (dt, J=14.7, 9.8 Hz, 1H), 2.55-2.47 (m, 1H), 2.33 (dt, J=16.0, 3.1 Hz, 1H), 1.68-1.60 (m, 1H), 1.28-1.17 (m, 1H). LCMS m/z (M+H)$^+$ 593.2.

Steps 4 and 5: Preparation of (3aR,9bR)-8-fluoro-7-(perfluoropropan-2-yl)-9b-(phenylsulfonyl)-2,3,3a,4,5,9b-hexahydro-1H-benzo[e]indole

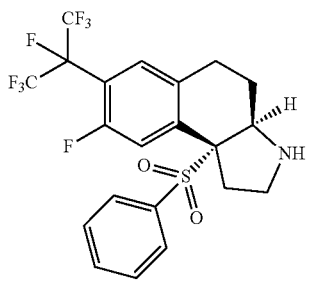 [SMILES: O=S(=O)(c1ccccc1)[C@@]12CCN[C@@H]1CCc1cc(C(F)(C(F)(F)F)C(F)(F)F)c(F)cc12]

To a suspension of 1-((3aR,9bR)-8-amino-7-(perfluoropropan-2-yl)-9b-(phenylsulfonyl)-1,2,3a,4,5,9b-hexahydro-3H-benzo[e]indol-3-yl)-2,2,2-trifluoroethan-1-one (2.00 g, 3.38 mmol) in DCM (40 mL) was added LiBF$_4$ (0.949 g, 10.1 mmol) and BF$_4$NO (0.591 g, 5.06 mmol) at 0° C. After stirring for 1.5 h at that temperature, the mixture was heated to 100° C. for 4.5 h in a sealed pressure flask. After cooling to rt, the mixture was filtered, the solid was washed several times with DCM and the filtrate and DCM washes were combined and concentrated under vacuum and purified by column chromatography on silica gel (40 g), eluting with DCM, to yield 2,2,2-trifluoro-1-((3aR,9bR)-8-fluoro-7-(perfluoropropan-2-yl)-9b-(phenylsulfonyl)-1,2,3a,4,5,9b-hexahydro-3H-benzo[e]indol-3-yl)ethan-1-one (1.30 g).

To a solution of this material in THF (16 mL), water (4 mL) and MeOH (4 mL) was added LiOH hydrate (0.916 g, 21.8 mmol) and the mixture was stirred at rt for 2 h. The reaction mixture was concentrated under vacuum, and the residue was diluted with water (30 mL) and saturated aqueous NaHCO$_3$ (10 mL) and extracted with DCM (2×60 mL). The combined organic phases were dried (Na$_2$SO$_4$) and concentrated under vacuum to yield (3aR,9bR)-8-fluoro-7-(perfluoropropan-2-yl)-9b-(phenylsulfonyl)-2,3,3a,4,5,9b-hexahydro-1H-benzo[e]indole (0.97 g, 58% yield over two steps, but contaminated with about 20% (3aR,9bR)-8-chloro-7-(perfluoropropan-2-yl)-9b-(phenylsulfonyl)-2,3,3a,4,5,9b-hexahydro-1H-benzo[e]indole) which was used without further purification.

Steps 6 and 7: Preparation of (1R,3S,4R)-4-((3aR,9bR)-8-fluoro-7-(perfluoropropan-2-yl)-9b-(phenylsulfonyl)-2,3,3a,4,5,9b-hexahydro-1H-benzo[e]indole-3-carbonyl)-3-methylcyclohexane-1-carboxylic acid To a solution of (3aR,9bR)-8-fluoro-7-(perfluoropropan-2-yl)-9b-(phenylsulfonyl)-2,3,3a,4,5,9b-hexahydro-1H-benzo[e]indole (0.95 g, 1.90 mmol) in N,N-dimethylformamide (10 mL) was added (1R,2S,4R)-4-(methoxycarbonyl)-2-methylcyclohexane-1-carboxylic acid (International Patent Application WO 2018/071620, 0.457 g, 2.28 mmol), HATU (0.940 g, 2.47 mmol) and diisopropylethylamine (0.997 mL, 5.71 mmol) at rt. The reaction mixture was stirred at rt for 1.5 h, quenched with saturated aqueous NH$_4$Cl (10 mL), diluted with water (50 mL), and extracted with EtOAc (3×50 mL). The combined organic phases were washed sequentially with saturated aqueous NH$_4$Cl (2×40 mL), saturated aqueous NaHCO$_3$ (50 mL), and brine (50 mL), dried (Na$_2$SO$_4$) and concentrated under vacuum. The residue was purified by column chromatography on silica gel (40 g), eluting with EtOAc/hexanes (gradient from 0-60% over 25 min), to provide methyl (1R,3S,4R)-4-((3aR,9bR)-8-fluoro-7-(perfluoropropan-2-yl)-9b-(phenylsulfonyl)-2,3,3a,4,5,9b-hexahydro-1H-benzo[e]indole-3-carbonyl)-3-methylcyclohexane-1-carboxylate.

To the above intermediate was added THF (8 mL), water (2.5 mL), MeOH (2.5 mL) and LiOH hydrate (0.798 g, 19.0 mmol) and the mixture was stirred at rt for 2 h. The reaction mixture was concentrated under reduced pressure, diluted with water (50 mL), acidified with 1 N aqueous HCl to pH 1, and extracted with EtOAc (2×50 mL). The combined organic phases were dried (Na$_2$SO$_4$) and concentrated under reduced pressure and the residue was subjected to SFC purification (Column: Chiral IC (4.6×25 cm, 5 micron); column temperature 40° C.; CO$_2$ flow rate: 3 mL/min; co-solvent: 0.1 NH$_4$OH in MeOH, flow rate 3 mL/min; injection volume: 10 mL) to afford (1R,3S,4R)-4-((3aR,9bR)-8-fluoro-7-(perfluoropropan-2-yl)-9b-(phenylsulfonyl)-2,3,3a,4,5,9b-hexahydro-1H-benzo[e]indole-3-carbonyl)-3-methylcyclohexane-1-carboxylic acid (730 mg, 58% yield, 98-99% pure). $^1$H NMR (500 MHz, methanol-d$_4$) δ 7.76 (d, J=13.1 Hz, 1H), 7.69-7.63 (m, 1H), 7.48-7.21 (m, 5H), 4.84-4.77 (m, 1H), 4.11 (s, 1H), 3.95-3.86 (m, 1H), 3.62-3.49 (m, 1H), 2.80-2.67 (m, 2H), 2.61-2.53 (m, 2H), 2.50-2.42 (m, 2H), 2.09-2.01 (m, 1H), 2.00-1.91 (m, 2H), 1.85-1.75 (m, 2H), 1.65-1.48 (m, 2H), 1.35-1.27 (m, 1H), 1.14-1.09 (m, 3H). LCMS m/z (M+H)$^+$ 668.3. HPLC (12 min gradient from 95:5 water/MeCN to 5:95 water/MeCN, with 0.05% TFA; flow rate 1 mL/min) t$_R$ 10.45 min, 99% purity (ACE UCore Super C$_{18}$ 2.5 μm, 3.0×125 mm), t$_R$ 9.62 min, purity 98.2% (ACE UCore SuperHexPh 2.5 μm, 3.0×125 mm). The absolute stereochemistry of the compound was determined based on single crystal X-ray analysis from the anomalous dispersion signal using the FLACK method.

General RORγ Gal4 Reporter Assay

Inverse agonist activity of potential ligands to RORγ was measured by inhibition of luminescence in a Gal4-luciferase reporter assay in Jurkat cells. urkat cells stably over-expressing the RORγ receptor, Jurkat pEx/Gal/hRORγ CLBD/HYG pG5luc/blast, were plated at a concentration of 10,000 cells/well in a 384-well solid white cell culture plate (Perkin Elmer #6007899) in assay buffer RPMI 1640 (Gibco 11875-085 1 L) containing 0.1% BSA, 100×HEPES (Gibco 15360-080), 100 mM sodium pyruvate (Gibco 11360-040), 50 mg/mL Hygromycin B (Invitrogen 10687-010) and 10 mg/mL blasticidin (Invitrogen R210-01). 100 nL of test compound in a 3-fold serial dilution, with final concentrations ranging from 40 μM to 0.67 nM, were added to the cells which were then incubated overnight.

The following day, cells were lysed with 10 μL of Steady-Glo Luciferase Assay System (Promega Cat. No. EZ550), and analyzed immediately. IC$_{50}$ values were determined. The IC$_{50}$ value is defined as the concentration of test compound needed to reduce luciferase activity by 50% and is calculated using the four parameter logistic equation to fit the normalized data.

IC$_{50}$ values for Compound 1 and for reference Compound A in the RORγ Gal4 reporter assay is provided below. Compound A is disclosed and claimed in U.S. Pat. No. 9,815,859.

| Ex. No. | RORγ Gal4 IC$_{50}$, μM |
|---|---|
| Compound 1 | 0.0036 |
| Compound A | 0.0025 |

Assay for Glutathione Conjugate formation in Rat or Human Cytosol Incubations

Compound A and Compound 1 were incubated at a concentration of 10 μM with rat or human liver cytosol (3-5 mg/mL) (male Sprague-Dawley rat liver cytosol, lot BIM, n=100 purchased from Bioreclamation IVT, or mixed gender pool, lot 452115, n=150 purchased from Corning) in 1 mL of potassium phosphate buffer (50 mM, pH 8.5). The reactions (n=2, total volume=1000 μL) were initiated by the addition of glutathione (GSH) (5 mM) and incubated at 37° C. in a thermomixer. At 0 and 60 min, aliquots (100 μL) of the reaction mixtures were collected, and reactions were terminated by adding two volumes of acetonitrile. Proteins were then removed using a Millipore Sigma (Massachusetts, BA) Multiscreen Solvinert filter plate, by centrifugation (Eppendorf 5810 R, Hamburg, Germany) at 2000 rpm for 5 min. The filtrate was collected in a 96-well plate and was analyzed by high resolution Velos LTQ-Orbitrap (LC-UV/MS) system. UV absorbance was collected from 220-600 nm. GSH conjugate identification was based on the observed accurate masses, MS fragmentation pattern was compared with those of the parent, obtained under comparable conditions to calculate peak area for parent compound and GSH conjugate.

The degrees of formation of GSH conjugates from the two compounds is shown below. Entries represent UV peak areas calculated relative to the parent compound at 260-280 nm. Data in parentheses represent the averages of the two experiments.

| | Rat Cytosol UV Area (%) | Human Cytosol UV Area (%) |
|---|---|---|
| Compound A | 14; 18 (~15%) | 4.5; 6 (~5%) |
| Compound 1 | not detected | not detected |

Compound Structures

Compound A

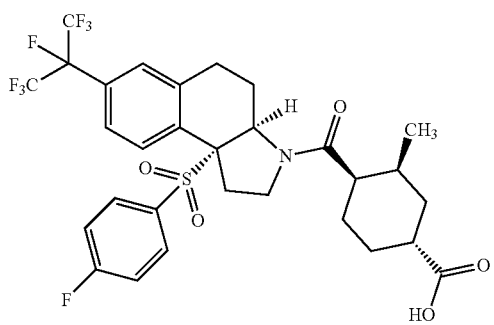

Compound 1

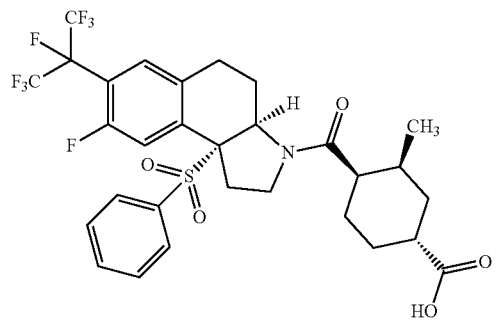

It was found that Compound 1 did not form a GSH adduct based on in vitro experiments.

What is claimed is:

1. A compound of the formula (I)

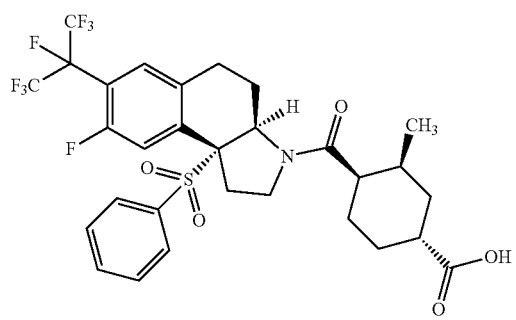

or a pharmaceutically acceptable salt thereof.

2. A compound of the formula (I)

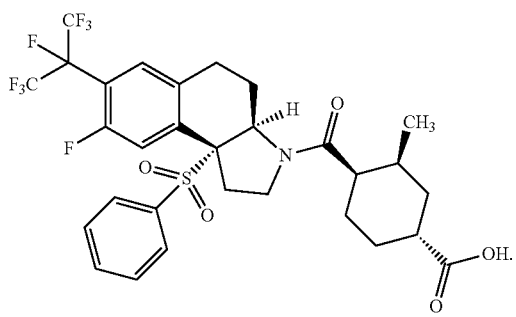

3. A pharmaceutical composition comprising the compound according to claim 1 and a pharmaceutically acceptable carrier or diluent.

4. A method of treating a disease or disorder modulated by RORγ, selected from an autoimmune disease or disorder, asthma, an allergic disease or disorder, a metabolic disease or disorder, and cancer in a subject, the method comprising administering to the subject a therapeutically-effective amount of the compound according to claim 1.

5. The method of claim 4 wherein the autoimmune disease or disorder is selected from psoriasis, rheumatoid arthritis, inflammatory bowel disease, Crohn's disease, ulcerative colitis, acute graft-versus-host disease, psoriatic arthritis, ankylosing spondylitis, systemic lupus erythematosus, lupus nephritis, Sjögren's syndrome, and multiple sclerosis.

\* \* \* \* \*